(12) United States Patent
Brandsborg

(10) Patent No.: US 11,077,154 B2
(45) Date of Patent: Aug. 3, 2021

(54) PROBIOTIC COMPOSITION AND USES THEREOF

(71) Applicant: Deerland Probiotics & Enzymes A/S, Hundested (DK)

(72) Inventor: Erik Brandsborg, Holbæk (DK)

(73) Assignee: Deerland Probiotics & Enzymes A/S, Hundested (DK)

( * ) Notice: Subject to any disclaimer, the term of this patent is extended or adjusted under 35 U.S.C. 154(b) by 0 days.

(21) Appl. No.: 16/099,987

(22) PCT Filed: May 9, 2017

(86) PCT No.: PCT/EP2017/061099
§ 371 (c)(1),
(2) Date: Nov. 8, 2018

(87) PCT Pub. No.: WO2017/194564
PCT Pub. Date: Nov. 16, 2017

(65) Prior Publication Data
US 2019/0134116 A1 May 9, 2019

(30) Foreign Application Priority Data
May 9, 2016 (EP) .................................... 16168814

(51) Int. Cl.
*A61K 35/747* (2015.01)
*C12N 1/20* (2006.01)
*C12R 1/225* (2006.01)
*A61P 1/02* (2006.01)

(52) U.S. Cl.
CPC .............. *A61K 35/747* (2013.01); *A61P 1/02* (2018.01); *C12N 1/20* (2013.01); *C12N 1/205* (2021.05); *C12R 1/225* (2013.01)

(58) Field of Classification Search
CPC combination set(s) only.
See application file for complete search history.

(56) References Cited

U.S. PATENT DOCUMENTS 9,308,227 B2 * 4/2016 Lang .................... A61K 35/744
2011/0104239 A1 5/2011 Knutsen et al.
2014/0065218 A1 3/2014 Lang et al.

FOREIGN PATENT DOCUMENTS

WO WO 2012/118535 A1 9/2012

OTHER PUBLICATIONS

Kõll-Klais, P. et al. "Oral lactobacilli in chronic periodontitis and periodontal health: species composition and antimicrobial activity" Oral Microbiology Immunology, 2005, pp. 354-361, vol. 20.
International Search Report for PCT/EP2017/061099 dated Jun. 21, 2017.

* cited by examiner

*Primary Examiner* — Heidi Reese
(74) *Attorney, Agent, or Firm* — Knobbe Martens Olson & Bear LLP

(57) ABSTRACT

The present invention relates to a *Lactobacillus curvatus* strain. In particular, the present invention relates to a composition comprising a *Lactobacillus curvatus* strain in combination with a further *Lactobacillus* and the use of the same in the treatment of inflammatory conditions in the oral cavity.

23 Claims, 11 Drawing Sheets

|  | DC -stimulation | | Th1-cocktail | | Th17-cocktail | | |
|---|---|---|---|---|---|---|---|
|  | Low IL-12 | High IL-10/IL-12 ratio | Low IL-12 | Increase in IL-10/IL-12 ratio | Low IL-23 | Increase in IL-10/IL-23 ratio | Total |
| S1P1 | 4 | 3 | 3 | 3 | 3 | 2 | 18 |
| S1P2 | 4 | 3 | 3 | 2 | 3 | 1 | 16 |
| S1P3 | 2 | 2 | 2 | 2 | 2 | 1 | 11 |
| DSM15224 | 0 | 1 | 0 | 4 | 2 | 4 | 11 |
| P2-1 | 3 | 2 | 2 | 1 | 3 | 1 | 12 |
| P2-2 | 4 | 4 | 4 | 4 | 4 | 4 | 24 |
| P2-3 | 3 | 3 | 1 | 3 | 2 | 2 | 14 |
| P3-1 | 4 | 4 | 4 | 4 | 3 | 2 | 21 |
| P3-2 | 4 | 3 | 3 | 4 | 3 | 3 | 20 |
| P5-1 | 2 | 1 | 1 | 2 | 1 | 1 | 8 |
| WCFS | 1 | 1 | 1 | 2 | 1 | 2 | 8 |
| PB01 | 3 | 2 | 3 | 2 | 3 | 2 | 15 |
| EB01 | 1 | 1 | 1 | 1 | 3 | 2 | 9 |
| LS33 | 3 | 2 | 2 | 2 | 3 | 3 | 15 |
| NCFM | 0 | 1 | 0 | 4 | 1 | 3 | 9 |

FIG 11

PROBIOTIC COMPOSITION AND USES THEREOF

CROSS REFERENCE TO RELATED APPLICATIONS

This application is a U.S. National Phase Application of PCT International Application Number PCT/EP2017/061099, filed on May 9, 2017, designating the United States of America and published in the English language, which is an International Application of and claims the benefit of priority to European Patent Application No. 16168814.8, filed on May 9, 2016. The disclosures of the above-referenced applications are hereby expressly incorporated by reference in their entireties.

FIELD OF THE INVENTION

The present invention relates to a *Lactobacillus curvatus* strain. In particular, the present invention relates to a composition comprising a *Lactobacillus curvatus* strain in combination with a further *Lactobacillus* and the use of the same in the treatment of inflammatory conditions in the oral cavity.

BACKGROUND OF THE INVENTION

The Human Microbiome Project has provided insights that the biofilms inside and outside our bodies have co-evolved with mankind and play an important role for health. This is also true for the oral cavity in which the microbiota does not play a passive role but actively contributes to the maintenance of oral health. However, certain ecological shifts in the microbiome allow pathogens to manifest and cause oral diseases. According to the ecological plaque hypothesis, caries and periodontitis are the result of environmentally induced overgrowth of aciduric and proteolytic species, respectively.

Bacteriotherapy is the term used when a harmless effector strain is implanted in the host's microflora to maintain or restore a natural microbiome by interference and/or inhibition of other microorganisms, and especially pathogens. This might open up alternative ways of fighting infectious diseases with less harmful side effects and may also help in the treatment of disorders that seem to have nothing to do with bacteria, such as asthma, obesity and diabetes. Probiotic bacteria, defined as "Live microorganisms which, when administered in adequate amounts, confer a health benefit on the host" (WHO), are commonly suggested candidates for bacteriotherapy. The potential mechanisms of action are still not fully understood but it seems clear that there are local (direct) as well as systemic (indirect) effects. According to Reid (2011) the potential avenues are: i) co-aggregation with pathogens and growth inhibition, ii) bacteriocin and hydrogen peroxide production, iii) competitive exclusion through antagonistic activities on adhesion sites and nutrition, iv) systemic immunomodulation.

In vitro studies have shown effect on co-aggregation and growth inhibition and clinical studies have shown effect on clinical parameters of gingival inflammation (Twetman, 2012) but still little is known about the immunomodulating effect in the oral cavity. Studies have however suggested that the proinflammtory cytokine TNF-α in gingival crevicular fluid can be reduced following short-term intake of probiotic lactobacilli (Twetman et al., 2009) and that the concentration secretory IgA may be up-regulated (Ericson et al., 2013).

Consequently, there is a need for compositions that contributes to the maintenance of oral health. In particular, there is a need for compositions that display immunomodulating effect in the oral cavity and may be used in the treatment and prevention of periodontal diseases such as gingival inflammation or periodontitis.

SUMMARY OF THE INVENTION

The present invention was made in view of the prior art described above, and the object of the present invention is to provide a probiotic composition, which may be used in the maintenance of oral health or in the prevention or treatment of inflammatory conditions in the oral cavity, such as gingival inflammation.

To solve the problem, the present invention provides compositions comprising *Lactobacillus curvatus* strain EB10 (DSM 32307) and methods of using the same. That is, the inventors of the present invention have found that the composition of the present invention comprising *Lactobacillus curvatus* strain EB10 (DSM 32307) is capable of inhibiting the growth pathogen bacterial strains known to be associated with periodontal diseases such as gingivitis. The composition of the present invention also displays a high ratio of IL10/12 in an in vitro assay on immature monocyte-derived dendritic cells. Data from an in vivo study demonstrate that the composition of the present invention comprising *Lactobacillus curvatus* strain EB10 (DSM 32307) reduces the volume of gingival crevicular fluid (GCF) over a period of 4 weeks. The in vivo study thus provides evidence that the composition of the present invention is capable of modulating at least one clinical marker of gingival inflammation.

A first aspect of the present invention provides *Lactobacillus curvatus* strain EB10. *Lactobacillus curvatus* strain EB10 (also referred to as P2-2 herein) was deposited with DSMZ-Deutsche Sammlung von Mikroorganismen and Zellkulturen GmbH (Inhoffenstr. 7 B, D-38124 Braunschweig, Germany) on 4 May 2016 for the purposes of patent deposit according to the Budapest Treaty. The deposit number of *Lactobacillus curvatus* strain EB10 is DSM 32307. Viability of the deposit was confirmed by the DSMZ on May 9, 2016.

A second aspect of the present invention relates to a culture comprising *Lactobacillus curvatus* strain EB10 (DSM 32307).

A third aspect of the present invention concerns a composition comprising *Lactobacillus curvatus* strain EB10 (DSM 32307).

A fourth aspect concerns a nutraceutical comprising the composition of the present invention.

A fifth aspect concerns a nutritional supplement comprising the composition of the present invention.

A six aspect of the present invention provides a container containing the composition of the present invention.

A seventh aspect of the present invention concerns a kit comprising a plurality of containers of the present invention.

A further aspect of the present invention provides a method for maintenance of oral health in a subject, said method comprising the step of providing a therapeutic effective amount of the composition of the present invention to a subject in the need thereof.

Yet a further aspect of the present invention provides a method for reducing gingival inflammation in a subject, said method comprising the step of
providing a therapeutic effective amount of the composition of the present invention to a subject in the need thereof.

BRIEF DESCRIPTION OF THE DRAWINGS

FIG. 11. The table shows the scoring of probiotic strains for clinical studies. Scores of individual probiotic strains in relation to the criteria defined in Example 6. The scale of the scoring goes from 0 to 4 and is defined as a relative score where 4 is best in relation to obtaining a potential anti-inflammatory effect.

DETAILED DESCRIPTION OF THE INVENTION

Figure 1:
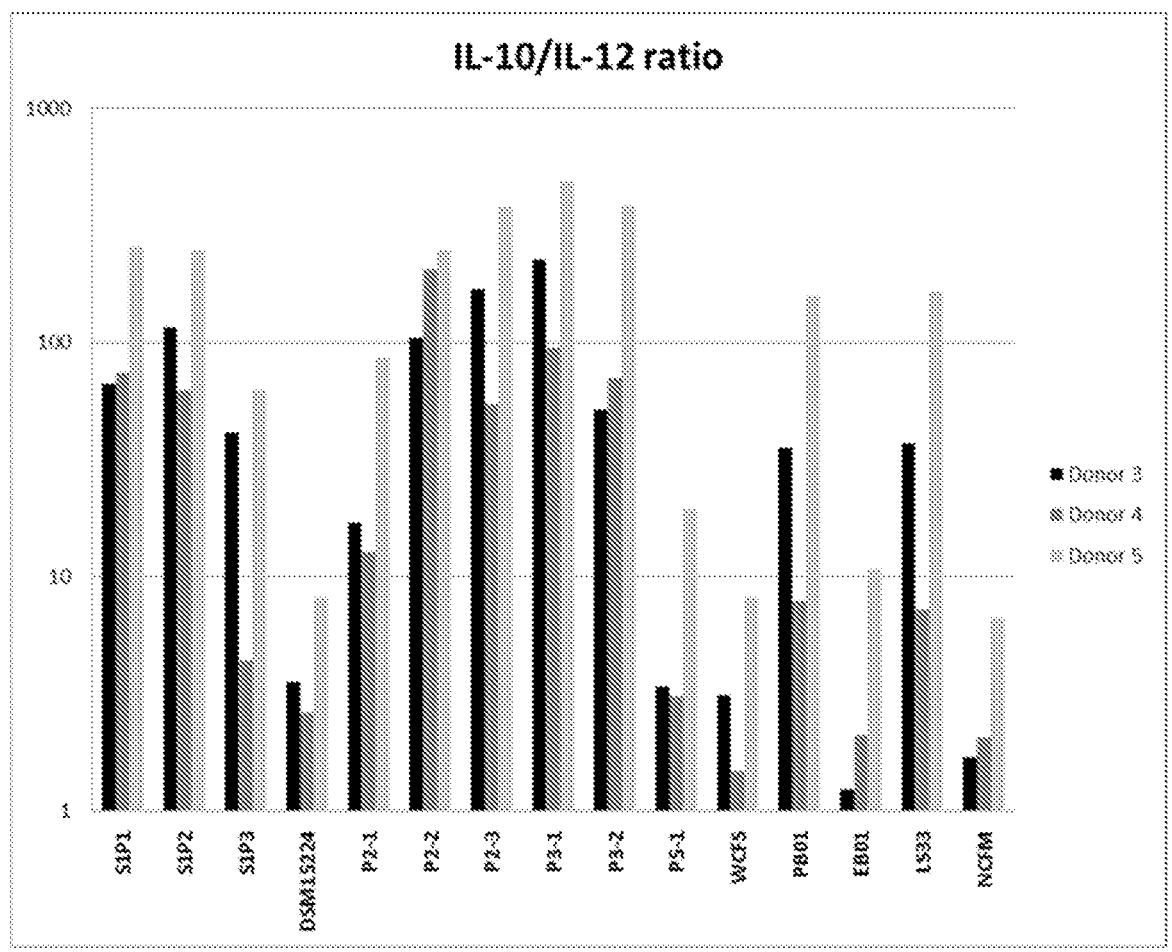
FIG. 1 shows the IL10/12 ratios of a panel of probiotic candidate strains obtained by assaying on immature monocyte-derived dendritic cells from three different donors (for further details see Example 3)

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

The inventor subjected a panel of candidate bacterial strains to agar overlay interference assay to identify bacterial strains among the candidates, which were capable of inhibiting the growth of pathogen bacterial strains known to be associated with periodontal diseases.

The panel of candidate bacterial strains included the bacterial strains S1-P1, S1-P2, S1-P3, P2-1, P2-2, P2-3, P3-1, P3-2, P5-1 was isolated from a mouth swap sample obtained from a healthy individual. The panel of candidate bacterial strains included further included DSM15224, *Lactobacillus plantarum* strain WCFS-1, *Lactobacillus gasseri* strain EB01 (DSM 14869) and *Lactobacillus salivarius* strain L33 JCM 1231 (ATCC SD5208) (See Example 1). The bacterial strain P2-2 is also referred to as *Lactobacillus curvatus* strain EB10 (DSM 32307).

The results of the agar overlay interference assay are disclosed in Example 2. The inventor discovered that several strains have the capacity of inhibiting the growth of the pathogen strains even if plated at low density ($10^1$ CFU).

The panel of candidate bacterial strains were subsequently to an in vitro immune modulation assay, wherein the candidate bacterial strains capacity to stimulate immature monocyte-derived dendritic cells to secrete IL-10 and IL-12 was assessed. A high ratio of IL10/12 may correlate with a protective effect against gingival inflammation. The probiotic bacterial strain *Lactobacillus acidophillus* NCFM (ATCC 700396) was included in the study as reference. The results of the immune modulation assay are disclosed in Example 3.

Nine strains out of the 14 strains assayed displayed a ratio of IL10/12 above 5 and four strains displayed a ratio of IL10/12 above 50. The inventor discovered that although several strains exhibit growth inhibition of pathogen bacterial strains known to be associated with periodontal diseases, this capacity does not necessarily correlate with a high ratio of IL10/12 and thus a protective effect against inflammation. For example, the candidate strains DSM15224, P5-1, WCFS-1 and L33 inhibits the growth of pathogen bacterial strains even when the candidate strains are plated at low density, but fails to display a high ratio of IL10/12 in the immune modulatory assay.

The strains *Lactobacillus curvatus* strain P3-1, *Lactobacillus curvatus* P2-2 (DSM 32307) and *Lactobacillus rhamnosus* PB01 (DSM 14870) were selected for further studies (Based on the scoring summarized in the table of FIG. 11). The inventor found that *Lactobacillus curvatus* strain P3-1 could not be produced in large scale for clinical testing and thus the further study was limited to *Lactobacillus rhamnosus* P2-2 (DSM 32307) and *Lactobacillus rhamnosus* PB01 (DSM 14870)

The bacterial strain *Lactobacillus curvatus* P2-2 (DSM 32307), also referred to as *Lactobacillus curvatus* strain EB10, was selected for clinical testing in combination with *Lactobacillus rhamnosus* PB01 (DSM 14870). The results of the clinical study is disclosed Example 4. The data demonstrate that the composition comprising *Lactobacillus curvatus* strain EB10 (DSM 32307) is capable of reducing the volume of gingival crevicular fluid (GCF), a clinical marker of gingival inflammation, over a period of 4 weeks. The clinical study thereby support the use a composition comprising *Lactobacillus curvatus* strain EB10 (DSM 32307) as an anti-inflammatory composition, which may be used in preventing or treating inflammatory conditions in the oral cavity, such as periodontal diseases, gingivitis in particular.

A first aspect of the present invention provides *Lactobacillus curvatus* strain EB10 (DSM 32307). The isolated *Lactobacillus curvatus* strain EB10 was deposited with DSMZ-Deutsche Sammlung von Mikroorganismen und Zellkulturen GmbH (Braunschweig, Germany) on 4 May 2016 for the purposes of patent deposit according to the Budapest Treaty. The *Lactobacillus curvatus* strain EB10 (DSM 32307) is also referred herein as *Lactobacillus curvatus* strain P2-2. 16S sequence analysis was performed using a PCR amplified fragment of the 16S rRNA gene of the strain. The sequence was blasted via NCBI to the sequence databases, which confirms that a 698 base sequence has 100% identity to *Lactobacillus curvatus* the 16S rRNA.

*Lactobacillus curvatus* EB10 (DSM 32307) was originally isolated from oral cavity, i.e. from the oral mucosa of healthy human donors *Lactobacillus curvatus* strain EB10 has been genetically characterized and appropriately classified as *Lactobacillus curvatus* by independent laboratories using the newest genotypic methods including 16S rRNA gene sequence analysis and PFGE regarding strain characterizing (See Example 6 for the PFGE data).

The morphology of *Lactobacillus curvatus* strain EB10 (DSM 32307) has been assessed using microscopy. *Lactobacillus curvatus* strain EB10 (DSM 32307) appears as flat grey colony. The cells are long rods forming chains of two or short chain of more cells, non-spore-forming.

In one embodiment, the isolated *Lactobacillus curvatus* strain EB10 (DSM 32307) is provided in its pure isolated form. In another embodiment, the *Lactobacillus curvatus* strain EB10 (DSM 32307) is provided in an essential isolated form.

A second aspect of the present invention provides a microbial culture, culture broth or ferment comprising the *Lactobacillus curvatus* strain EB10 (DSM 32307) of the present invention. The *Lactobacillus curvatus* strain EB10 (DSM 32307) cells comprised in the microbial culture, culture broth or ferment are initially essentially all viable. By essentially all viable means that at least 50% of the bacteria present in microbial culture, culture broth or ferment immediately after the preparation of the same are viable, such as at least 75%, for example at least 85%, such as at least 90%, for example at least 95%.

The viability of the bacteria may be confirmed by plating the bacteria on a suitable medium (e.g. solidified agar in a standard sized Petri dish) and determine the number of colonies formed. The measure, colony forming unit (or CFU), is used quantify the amount of viable (live) bacteria in the composition (reflecting the capacity of the bacteria to replicate).

The bacteria comprised in the microbial culture, culture broth, ferment and composition of the present invention confers a health benefit to the subject, when ingested in adequate amounts by a subject (such as in the form a formulation as described herein). It follows that the bacteria is non-pathogenic and does not confer any harmful effect in the ingested amounts. The bacteria are also referred to as probiotic bacteria.

In one embodiment of the present invention, the microbial culture, culture broth or ferment is a pure or essentially pure, in the sense that the only or essentially only organism present is *Lactobacillus curvatus* strain EB10 (DSM 32307).

In another embodiment, the microbial culture, culture broth or ferment comprises at least one further probiotic microorganism, preferably a probiotic bacterium. Preferably the at least further probiotic bacterium is a *Lactobacillus* sp. More preferably, the microbial culture, culture broth or ferment comprises *Lactobacillus rhamnosus* strain PB01 (DSM 14870). In yet another embodiment, the microbial culture, culture broth or ferment further comprises *Lactobacillus salivarius* strain LS33 (ATCC SD5208). In one embodiment, bacteria present in the microbial culture, culture broth or ferment consists essentially of *Lactobacillus curvatus* strain EB10 (DSM 32307), *Lactobacillus curvatus* strain EB10 (DSM 32307) and *Lactobacillus rhamnosus* strain PB01 (DSM 14870), *Lactobacillus curvatus* strain EB10 (DSM 32307) and *Lactobacillus salivarius* strain LS33 (ATCC SD5208) or *Lactobacillus curvatus* strain EB10 (DSM 32307) and *Lactobacillus rhamnosus* strain PB01 (DSM 14870) and *Lactobacillus salivarius* strain LS33 (ATCC SD5208). The microbes present in the microbial culture, culture broth or ferment are preferably balanced such that *Lactobacillus curvatus* strain EB10 (DSM 32307) is not outnumbered by other bacteria included in the microbial culture, culture broth or ferment. For example, the CFU in the microbial culture, culture broth or ferment may be evenly distributed between the microbes present.

In another embodiment, at least 50% of CFU is *Lactobacillus curvatus* strain EB10 (DSM 32307), such as at least 60%, for example at least 70%, such as at least 80%, for example at least 90%, such as at least 95% of CFU is *Lactobacillus curvatus* strain EB10 (DSM 32307). In a further embodiment, about 50% of CFU is *Lactobacillus curvatus* strain EB10 (DSM 32307) and about 50% of CFU is *Lactobacillus rhamnosus* strain PB01 (DSM 14870). In yet a further embodiment, about 50% of CFU is *Lactobacillus curvatus* strain EB10 (DSM 32307) and about 50% of CFU is *Lactobacillus salivarius* strain LS33 (ATCC SD5208).

A third aspect provides composition comprising *Lactobacillus curvatus* strain EB10 (DSM 32307). In one embodiment of the present invention, the composition is a pure or essentially pure, in the sense that the only or essentially only organism present is *Lactobacillus curvatus* strain EB10 (DSM 32307).

In another embodiment, the composition comprises at least one further probiotic microorganism, preferably a probiotic bacterium. Preferably the at least further probiotic bacterium is a *Lactobacillus* sp. More preferably, the composition comprises *Lactobacillus rhamnosus* strain PB01 (DSM 14870). In yet another embodiment, the composition further comprises *Lactobacillus salivarius* strain LS33 (ATCC SD5208). In one embodiment, bacteria present in the composition consists essentially of *Lactobacillus curvatus* strain EB10 (DSM 32307), *Lactobacillus curvatus* strain EB10 (DSM 32307) and *Lactobacillus rhamnosus* strain PB01 (DSM 14870), *Lactobacillus curvatus* strain EB10 (DSM 32307) and *Lactobacillus salivarius* strain LS33 (ATCC SD5208) or *Lactobacillus curvatus* strain EB10 (DSM 32307) and *Lactobacillus rhamnosus* strain PB01 (DSM 14870) and *Lactobacillus salivarius* strain LS33 (ATCC SD5208). The microbes present in the composition are preferably balanced such that *Lactobacillus curvatus* strain EB10 (DSM 32307) is not outnumbered by other bacteria included in the composition. For example, the CFU in the composition may be evenly distributed between the microbes present.

In another embodiment, at least 50% of CFU is *Lactobacillus curvatus* strain EB10 (DSM 32307), such as at least 60%, for example at least 70%, such as at least 80%, for example at least 90%, such as at least 95% of CFU is

*Lactobacillus curvatus* strain EB10 (DSM 32307). In a further embodiment, about 50% of CFU is *Lactobacillus curvatus* strain EB10 (DSM 32307) and about 50% of CFU is *Lactobacillus rhamnosus* strain PB01 (DSM 14870). In yet a further embodiment, about 50% of CFU is *Lactobacillus curvatus* strain EB10 (DSM 32307) and about 50% of CFU is *Lactobacillus salivarius* strain LS33 (ATCC SD5208).

The initial colony forming units (CFU) and the continued stability and viability of the composition is influenced by a variety of factors. The stability of a probiotic composition tested at the time of manufacture will depend on a combination of factors. Variations in packaging, temperature, and humidity will affect the viability of probiotic products before they are taken. Protective factors that help to preserve the freshness and viability of the probiotic strains in a supplement include refrigeration, resistant packaging, and storage in a cool, dry place. If a probiotic composition is held in conditions that are very warm or moist, the CFU in the composition declines. Thus, the continued stability and viability is dependent on limiting their exposure to stimulating environmental conditions such as warmth and moisture.

In one embodiment of the present invention, the composition comprises at least $10^5$ CFU of *Lactobacillus* per gram of said composition, such as at least $10^6$ CFU of *Lactobacillus* per gram of said composition, for example at least $10^7$ CFU of *Lactobacillus* per gram of said composition, such as at least $10^8$ CFU of *Lactobacillus* per gram of said composition, for example at least $10^9$ CFU of *Lactobacillus* per gram of said composition, such as at least $10^{10}$ CFU of *Lactobacillus* per gram of said composition.

In one embodiment of the present invention, the composition comprises from $10^5$ to $10^{13}$ CFU of *Lactobacillus* per gram of said composition. In another embodiment of the present invention, the composition comprises from $10^6$ to $10^{12}$ CFU of *Lactobacillus* per gram of said composition. In yet another embodiment, the composition comprises from $10^7$ to $10^{11}$ CFU of *Lactobacillus* per gram of said composition. In a further embodiment, the composition comprises from $10^8$ to $10^{10}$ CFU of *Lactobacillus* per gram of said composition, such as $10^9$ *Lactobacillus* per gram of said composition.

In a preferred embodiment, the composition comprises *Lactobacillus curvatus* strain EB10 (DSM 32307) and *Lactobacillus rhamnosus* strain PB01 (DSM 14870). In one embodiment, the composition comprises at least $10^7$ CFU *Lactobacillus curvatus* strain EB10 (DSM 32307) per gram of said composition, such as at least $10^8$ CFU *Lactobacillus curvatus* strain EB10 (DSM 32307) per gram of said composition, for example at least $10^9$ CFU *Lactobacillus curvatus* strain EB10 (DSM 32307) per gram of said composition, such as at least $10^{10}$ CFU *Lactobacillus curvatus* strain EB10 (DSM 32307) per gram of said composition.

In a further embodiment, the composition further comprises *Lactobacillus rhamnosus* strain PB01 (DSM 14870), for example at least $10^7$ CFU *Lactobacillus rhamnosus* strain PB01 (DSM 14870) per gram of said composition, such as at least $10^8$ CFU *Lactobacillus rhamnosus* strain PB01 (DSM 14870) per gram of said composition, for example at least $10^9$ CFU *Lactobacillus rhamnosus* strain PB01 (DSM 14870) per gram of said composition, such as at least $10^{10}$ CFU *Lactobacillus rhamnosus* strain PB01 (DSM 14870) per gram of said composition.

In yet a further embodiment, the composition further comprises *Lactobacillus salivarius* strain LS33 (ATCC SD5208), for example at least $10^7$ CFU *Lactobacillus salivarius* strain LS33 (ATCC SD5208) per gram of said composition, such as at least $10^8$ CFU *Lactobacillus salivarius* strain LS33 (ATCC SD5208) per gram of said composition, for example at least $10^9$ CFU *Lactobacillus salivarius* strain LS33 (ATCC SD5208) per gram of said composition, such as at least $10^{10}$ CFU *Lactobacillus salivarius* strain LS33 (ATCC SD5208) per gram of said composition.

The *Lactobacillus* strains of the composition of the present invention may be provided in any suitable form depending on the formulation of the composition. In a preferred embodiment, the *Lactobacillus* is in a lyophilized or spray dried form.

Excipients

In one embodiment of the present invention, the composition further comprises at least one excipient. In another embodiment, the at least one excipient is selected from the group consisting of a bulking agent, a binder, a glazing agent, a sweetener and a flavour.

In the context of the present invention, the term "bulking agent" refers to an additive that increases the volume or weight of the composition while keeping its utility or functionality intact. In one embodiment of the present invention, the composition comprises at least one bulking agent selected from the group consisting of xylitol, sorbitol, erythritol, maltitol, lactitol, inositol and mannitol microcrystalline cellulose and isomalt.

In the context of the present invention, the term "binder" refers to binding material that keeps components of the composition together, stabilizes a form or shape, or causes a mixture to coalesce. In one embodiment of the present invention, the composition comprises at least one binder selected from the group consisting of maltodextrin and sodium carboxymethylcellulose.

In the context of the present invention, the term "glazing agent" refers to a natural or synthetic substance that provides a waxy, homogeneous, coating to provide protection to the composition. In one embodiment of the present invention, the composition comprises at least one glazing agent selected from the group consisting of mono- and diglyceride of fatty acids, silicon dioxide, stearic acid, beeswax, candelilla wax, carnauba wax, shellac, microcrystalline wax, crystalline wax, lanolin, oxidized polyethylene wax, esters of colophonium, paraffin.

The composition of the present invention may further comprise at least one sweetener. In one embodiment, the at least one sweetener is a low calorie sweetener.

In one embodiment, the low calorie sweetener is selected from the list consisting of a bulk sweetener and an intense sweetener. In yet an embodiment, the low calorie sweetener is a sugar alcohol. In a further embodiment, the low calorie sweetener is selected from the list consisting of xylitol, sorbitol, erythritol, maltitol, lactitol, isomalt, inositol and mannitol.

The composition may comprise a combination of low calorie sweetener such as a combination of sugar alcohols a described above. Alternatively, the composition may also comprise a combination of one or more bulk sweetener and one or more intense sweeteners.

In one embodiment, the composition comprises an intense sweetener selected from the list consisting of saccharin, aspartame, stevia, a steviol glycoside such as stevioside, sucralose and acesulfame such as acesulfame potassium (Ace-K). In another embodiment, the sweetener is selected from the group consisting of rebaudioside, aspartame, neotame, saccharin, and advantame.

The composition of the present invention comprises at least one flavour. More than one flavour may be included to provide a more complex tasting experience. In one embodiment, said at least one flavour is at least one flavour selected from the group consisting of citric acid, lemon flavour, honeydew melon flavour, blueberry flavour, peach flavour, strawberry flavour, raspberry flavour, cola flavour, chocolate flavour, peppermint flavour, cherry flavour, lime flavour, orange flavour, vanilla flavour, tangerine flavour, liquorice flavour, apricot flavour, eucalyptus flavour, green tea flavour, ginger flavour and bilberry flavour. The amount of flavour compounds in the composition may vary. In one embodiment, the at least one flavour is present in an amount from 1 to 10% w/w in said composition.

In a preferred embodiment, the composition of the invention comprises:
 (i) bulking agents in the form of xylitol and microcrystalline cellulose, isomalt,
 (ii) binders in the form of maltodextrin and sodium carboxymethylcellulose,
 (iii) glazing agents in the form of mono- and diglyceride of fatty acids and silicon dioxide,
 (iv) a sweetener in the form of steviol glycoside, and
 (v) flavours in the form of citric acid and lemon flavour.

The composition may also comprise a prebiotic that stimulates the proliferation of the microorganism in the GI of the subject ingesting the composition. In one embodiment, the composition further comprises at least one prebiotic selected from the group consisting of sialo-oligosaccharides (SOS), fructo-oligosaccharides (FOS), galacto-oligosaccharides (GOS), isomalto-oligosaccharides (IMO), xylo-oligosaccharides (XOS), arabino-xylo oligosaccharides (AXOS), mannan oligosaccharides (MOS), oligosaccharides of soy, glycosylsucrose (GS), lactosucrose (LS), sialyl-lactose (SL) Fucosyl-lactose (FL), Lacto-N-Neotetraose (LNNT), lactulose (LA), palatinose-oligosaccharides (PAO), malto-oligosaccharides, gums and/or hydrolysates thereof, pectins, starches, and/or hydrolysates thereof.

Formulation of the Composition of the Invention

The composition may be provided in any suitable formulation. Preferably, the composition is provided in a formulation suitable for oral administration. In one embodiment, the composition is in the form of a tablet, a capsule, powder, effervescent tablet, effervescent powder, granulate, a microencapsulated product, a suspension, spray, a gel or a cream. In a preferred embodiment, the composition is formulated as a tablet, preferably a chewable tablet.

In one embodiment, the composition of the present invention is formulated as a pharmaceutical composition, which comprises at least one pharmaceutically acceptable excipient or carrier.

Use of the Composition of the Invention

One aspect of the present invention provides the composition for use as a medicament. The inventor has discovered that the composition of the present invention is capable of reducing the volume of gingival crevicular fluid (GCF), a clinical marker of gingival inflammation, over a period of 4 weeks. The in vitro study further demonstrates that the composition of the present invention display a high ratio of IL10/12, which suggests a protective effect against inflammation such as gingival inflammation.

The data provided thus support the use a composition comprising Lactobacillus curvatus strain EB10 (DSM 32307) as an anti-inflammatory composition, which may be used in preventing or treating inflammatory conditions in the oral cavity, such as periodontal diseases, gingivitis in particular.

Thus, aspect of the present invention relates to the composition of the present invention for use in the treatment of an inflammatory condition. In one embodiment, the said inflammatory disease is an inflammatory condition in the oral cavity. In a further embodiment, the inflammatory condition is periodontal diseases such as gingivitis or periodontitis. In a preferred embodiment, the inflammatory condition is gingivitis.

The composition may be for administration as a once daily dose. The composition may thus be formulated accordingly, e.g. as a one daily dose unit. The composition may also be for administration as a twice daily dose, three times daily dose or even for administration several times daily. It follows that the composition may thus be formulated according to the dosage regimen. In one embodiment of the present invention, the composition is administrated twice daily.

In one embodiment, the composition comprises at least $10^7$ CFU Lactobacillus per daily dose, such as in the range of $10^7$ to $10^{10}$ CFU Lactobacillus per daily dose, such as $10^8$ to $10^9$ CFU Lactobacillus per daily dose.

In one embodiment, the composition comprises at least $10^7$ CFU Lactobacillus curvatus strain EB10 (DSM 32307) per daily dose, for example at least $5\times10^7$ CFU Lactobacillus curvatus strain EB10 per daily dose, such as in the range of $10^7$ to $10^{10}$ CFU Lactobacillus curvatus strain EB10 per daily dose, such as $10^8$ to $10^9$ CFU Lactobacillus curvatus strain EB10 per daily dose.

In another embodiment, the composition further comprises Lactobacillus rhamnosus strain PB01 (DSM 14870). In one embodiment, the composition further comprises at least $10^7$ CFU Lactobacillus rhamnosus strain PB01 (DSM 14870) per daily dose, for example at least $5\times10^7$ CFU Lactobacillus rhamnosus strain PB01 (DSM 14870) per daily dose, such as in the range of $10^7$ to $10^{10}$ CFU Lactobacillus rhamnosus strain PB01 (DSM 14870) per daily dose, such as $10^8$ to $10^9$ CFU Lactobacillus rhamnosus strain PB01 (DSM 14870) per daily dose.

In one embodiment, the composition comprises at least $10^7$ CFU Lactobacillus curvatus strain EB10 (DSM 32307) per daily dose, such as at least $5\times10^7$ CFU Lactobacillus curvatus strain EB10 per daily dose and at least $1\times10^7$ CFU Lactobacillus rhamnosus strain PB01 (DSM 14870) per daily dose, such as at least $5\times10^7$ CFU Lactobacillus rhamnosus strain PB01 (DSM 14870) per daily dose.

In another embodiment, the composition further comprises Lactobacillus salivarius strain LS33 (ATCC SD5208). In one embodiment, the composition further comprises at least $10^7$ CFU Lactobacillus salivarius strain LS33 (ATCC SD5208) per daily dose, for example at least $5\times10^7$ CFU Lactobacillus salivarius strain LS33 (ATCC SD5208) per daily dose, such as in the range of $10^7$ to $10^{10}$ CFU Lactobacillus salivarius strain LS33 (ATCC SD5208) per daily dose, such as $10^8$ to $10^9$ CFU Lactobacillus salivarius strain LS33 (ATCC SD5208) per daily dose.

In one embodiment, the composition comprises at least $10^7$ CFU Lactobacillus salivarius strain LS33 (ATCC SD5208) per daily dose, such as at least $5\times10^7$ CFU Lactobacillus salivarius strain LS33 (ATCC SD5208) per daily dose and at least $1\times10^7$ CFU Lactobacillus salivarius strain LS33 (ATCC SD5208) per daily dose, such as at least $5\times10^7$ CFU Lactobacillus salivarius strain LS33 (ATCC SD5208) per daily dose.

In one embodiment, the composition comprises at least $10^7$ CFU Lactobacillus curvatus strain EB10 (DSM 32307) per daily dose, such as at least $5\times10^7$ CFU Lactobacillus curvatus strain EB10 per daily dose and at least $1\times10^7$ CFU Lactobacillus salivarius strain LS33 (ATCC SD5208) per daily dose, such as at least $5\times10^7$ CFU Lactobacillus salivarius strain LS33 (ATCC SD5208) per daily dose.

In one embodiment of the present invention, the composition for the use according to the present invention is administrated orally. For this purpose, the composition may be provided in the form of a tablet, a capsule, powder, effervescent tablet, effervescent powder, granulate, a microencapsulated product, a suspension, spray, a gel or a cream. In a preferred embodiment, the composition is formulated as a tablet, preferably a chewable tablet.

One aspect of the present invention concerns a method for maintenance of oral health in a subject, said method comprising the step of
providing a therapeutic effective amount of a composition according to the present invention to a subject in the need thereof.

Another aspect of the present invention concerns a method for reducing gingival inflammation in a subject, said method comprising the step of
providing a therapeutic effective amount of a composition according to the present invention to a subject in the need thereof.

Yet another aspect of the present invention concerns a method for reducing the volume of gingival crevicular fluid (GCF) in a subject, said method comprising the step of
providing a therapeutic effective amount of a composition according to the present invention to a subject in the need thereof.

In one embodiment, the methods include a further step of taking samples and monitoring the volume of gingival crevicular fluid (GCF) during the treatment, e.g. by reference to the volume of gingival crevicular fluid (GCF) before the onset of the treatment.

The above methods preferably comprise daily administration of the composition of the present invention. In one embodiment, the composition provided to the subject comprises at least $10^7$ CFU *Lactobacillus* per daily dose, such as in the range of $10^7$ to $10^{10}$ CFU *Lactobacillus* per daily dose, such as $10^8$ to $10^9$ CFU *Lactobacillus* per daily dose.

In one embodiment, the composition comprises at least $10^7$ CFU *Lactobacillus curvatus* strain EB10 (DSM 32307) per daily dose, for example at least $5\times10^7$ CFU *Lactobacillus curvatus* strain EB10 per daily dose, such as in the range of $10^7$ to $10^{10}$ CFU *Lactobacillus curvatus* strain EB10 per daily dose, such as $10^8$ to $10^9$ CFU *Lactobacillus curvatus* strain EB10 per daily dose.

In another embodiment, the composition further comprises *Lactobacillus rhamnosus* strain PB01 (DSM 14870). In one embodiment, the composition further comprises at least $10^7$ CFU *Lactobacillus rhamnosus* strain PB01 (DSM 14870) per daily dose, for example at least $5\times10^7$ CFU *Lactobacillus Rhamnosus* strain PB01 (DSM 14870) per daily dose, such as in the range of $10^7$ to $10^{10}$ CFU *Lactobacillus rhamnosus* strain PB01 (DSM 14870) per daily dose, such as $10^8$ to $10^9$ CFU *Lactobacillus rhamnosus* strain PB01 (DSM 14870) per daily dose.

In one embodiment, the composition comprises at least $10^7$ CFU *Lactobacillus curvatus* strain EB10 (DSM 32307) per daily dose, such as at least $5\times10^7$ CFU *Lactobacillus curvatus* strain EB10 per daily dose and at least $1\times10^7$ CFU *Lactobacillus Rhamnosus* strain PB01 (DSM 14870) per daily dose, such as at least $5\times10^7$ CFU *Lactobacillus Rhamnosus* strain PB01 (DSM 14870) per daily dose.

Supplements

In the context of the present invention a nutritional supplement (or a dietary supplement) is a product intended for ingestion that contains a "dietary ingredient" intended to add further nutritional value to (supplement) the diet.

One aspect of the present invention provides a nutritional supplement comprising the composition of the present invention.

In the context of the present invention, the term "nutraceuticals" refers to a product derived from food sources with the extra health benefits described herein in addition to the basic nutritional value found in foods. The nutraceuticals of the present invention may contribute to the maintenance of oral health in a subject and reduce the risk of obtaining an inflammatory condition in the mouth cavity, such as a periodontal disease, for example gingivitis. The nutraceuticals of the present invention may also reduce the volume of gingival crevicular fluid (GCF), a clinical marker of gingival inflammation and thus contribute to the prevention or treatment of gingival inflammation.

One aspect of the present invention provides a nutraceutical comprising the composition of the present invention. In one embodiment, the nutraceutical is provided in the form of a functional food. Functional food is a category which includes whole foods and fortified with the composition of the present invention. In another embodiment, the nutraceutical is provided in the form of a medical food. The medical food is formulated to be consumed or administered internally, under the supervision of a qualified physician. The nutritional supplement may be provided in many forms such as tablets (such as chewable tablet), effervescent tablet, effervescent powder, capsules, softgels, gelcaps, liquids, or powders.

The nutritional supplement of the present invention may contribute to the maintenance of oral health in a subject and reduce the risk of obtaining an inflammatory condition in the mouth cavity, such as a periodontal disease, for example gingivitis. The nutritional supplement of the present invention may also reduce the volume of gingival crevicular fluid (GCF), a clinical marker of gingival inflammation and thus contribute to the prevention or treatment of gingival inflammation.

Packaging

The composition of the present invention is typically filled in a container, which is preferably sealed, which provide an oxygen and moisture barrier in order to maintain the integrity of the composition.

Accordingly, one aspect of the present invention concerns a container containing the composition of the present invention. Non limiting examples of suitable containers include a blister pack (such as a blister pack of tablets), a stick, bag, pouch or capsule. In a preferred embodiment, the container is an aluminium foil or a polyethylene stick, which is typically sealed by welding. The stick is typically configured for easy tear opening. The stick may have a tear notch. Thus, the stick may be discarded after ingestion of the composition. Preferably, the container, such as in the form of a stick or blister pack of tablets, comprises a single dose of the composition.

The container may comprise desiccant to that induces or sustains a state of dryness (desiccation) of the composition. The desiccants may be in forms other than solid, and may work through other principles, such as chemical bonding of water molecules.

The desiccant many be any desiccant suitable for food or pharmaceutical applications. Examples of desiccant include silica, charcoal and molecular sieves.

In a further aspect of the present invention a kit is provided, wherein said kit comprises a plurality of containers each comprising the composition of the present invention. Preferably, each container of the kit comprises a single dose of the composition. Every container of the kit may comprise the same composition. Alternatively, the containers may comprise different compositions, e.g. the compositions may comprise different flavours.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and "comprises" herein are intended by the inventors to be optionally substitutable with the terms "consisting of", "consist of" and "consists of", respectively, in every instance.

The present invention is further described in the following non-limiting items:

Item 1. *Lactobacillus curvatus* strain EB10 (DSM 32307).

Item 2. A culture comprising *Lactobacillus curvatus* strain EB10 (DSM 32307).

Item 3. The culture according to item 2 comprising at least one further *Lactobacillus* sp.

Item 4. The culture according to item 2 or 3 further comprising *Lactobacillus rhamnosus* strain PB01 (DSM 14870).

Item 5. A composition comprising *Lactobacillus curvatus* strain EB10 (DSM 32307).

Item 6. The composition according to item 5 comprising at least one further *Lactobacillus* sp.

Item 7. The composition according to item 5 or 6 further comprising *Lactobacillus rhamnosus* strain PB01 (DSM 14870).

Item 8. The composition according to item 6 or 7, wherein said composition comprises from $10^5$ to $10^{13}$ CFU of *Lactobacillus* per gram of said composition.

Item 9. The composition according to any one of items 5 to 8, wherein said composition comprises from $10^6$ to $10^{12}$ CFU of *Lactobacillus* per gram of said composition.

Item 10. The composition according to any one of items 5 to 9, wherein said composition comprises from $10^7$ to $10^{11}$ CFU of *Lactobacillus* per gram of said composition.

Item 11. The composition according to any one of items 5 to 10, wherein said composition comprises from $10^8$ to $10^{10}$ CFU of *Lactobacillus* per gram of said composition, such as $10^9$ *Lactobacillus* per gram of said composition.

Item 12. The composition according to any one of items 5 to 11 comprising *Lactobacillus curvatus* strain EB10 (DSM 32307) and *Lactobacillus rhamnosus* strain PB01 (DSM 14870).

Item 13. The composition according to any one of items 5 to 12 comprising at least $10^7$ CFU *Lactobacillus curvatus* strain EB10 (DSM 32307) per gram of said composition.

Item 14. The composition according to item 13 comprising at least $10^7$ CFU *Lactobacillus rhamnosus* strain PB01 (DSM 14870) per gram of said composition.

Item 15. The composition according to any one of the preceding items, wherein said *Lactobacillus* is in a lyophilized or spray dried form.

Item 16. The composition according to any one of the preceding items further comprising at least one excipient.

Item 17. The composition according to item 16, wherein said at least one excipient is selected from the group consisting of a bulking agent, a binder, a glazing agent, a sweetener and a flavour.

Item 18. The composition according to item 17, wherein said bulking agent is at least one bulking agent selected from the group consisting of xylitol, sorbitol, erythritol, maltitol, lactitol, inositol and mannitol microcrystalline cellulose and isomalt.

Item 19. The composition according to item 17 or 18, wherein said binder is at least one binder selected from the group consisting of maltodextrin and sodium carboxymethylcellulose.

Item 20. The composition according to any one of items 17 to 19, wherein said glazing agent is at least one glazing agent selected from the group consisting of mono- and diglyceride of fatty acids, silicon dioxide, stearic acid, beeswax, candelilla wax, carnauba wax, shellac, microcrystalline wax, crystalline wax, lanolin, oxidized polyethylene wax, esters of colophonium, paraffin.

Item 21. The composition according to any one of items 17 to 20, wherein said sweetener is at least one sweetener selected from the group consisting of stevia, a steviol glycoside such as stevioside and rebaudioside, aspartame, sucralose, neotame, acesulfame potassium (Ace-K), saccharin, and advantame.

Item 22. The composition according to any one of items 17 to 21, wherein said flavour is at least one flavour selected from the group consisting of citric acid, lemon flavour, honeydew melon flavour, blueberry flavour, peach flavour, strawberry flavour, raspberry flavour, cola flavour, chocolate flavour, peppermint flavour, cherry flavour, lime flavour, orange flavour, vanilla flavour, tangerine flavour, liquorice flavour, apricot flavour, eucalyptus flavour, green tea flavour, ginger flavour and bilberry flavour.

Item 22. The composition according to any one of the preceding items, comprising:
  (i) bulking agents in the form of xylitol and microcrystalline cellulose, isomalt,
  (ii) binders in the form of maltodextrin and sodium carboxymethylcellulose,
  (iii) glazing agents in the form of mono- and diglyceride of fatty acids and silicon dioxide,
  (iv) a sweetener in the form of steviol glycoside, and
  (v) flavours in the form of citric acid and lemon flavour.

Item 23. The composition according to any one of the preceding items, wherein said composition is in the form of a tablet, a capsule, powder, effervescents tablet, effervescents powder, a granulate, a microencapsulated product, a suspension, spray, a gel or a cream.

Item 24. The composition according to any one of the preceding items for use as a medicament.

Item 25. The composition according to any one of the preceding items for use in the treatment of an inflammatory condition.

Item 26. The composition for use according to item 25, wherein said inflammatory disease is an inflammatory condition in the oral cavity.

Item 27. The composition for use according to item 25, wherein said inflammatory condition is periodontal diseases such as gingivitis or periodontitis.

Item 28. The composition for use according to any of items 24 to 27, wherein said composition comprises from $10^7$ to $10^{10}$ CFU *Lactobacillus* per daily dose, such as $10^8$ to $10^9$ CFU *Lactobacillus* per daily dose.

Item 29. The composition for use according to item 28, wherein said composition comprises at least $5\times10^7$ CFU *Lactobacillus curvatus* strain EB10 (DSM 32307) per daily dose.

Item 30. The composition for use according to item 28 or 29, wherein said composition comprises at least $5\times10^7$ CFU *Lactobacillus rhamnosus* strain PB01 (DSM 14870) per daily dose.

Item 31. The composition for use according to any of items 24 to 30, wherein the composition is administrated twice daily.

Item 32. The composition for use according to any of items 24 to 31, wherein the composition is administrated orally.

Item 33. A nutraceutical comprising the composition according to any one of the preceding items.

Item 34. A nutritional supplement comprising the composition according to any one of the preceding items.

Item 35. A container containing the composition according to any one of the preceding items.

Item 36. The container according to item 35, wherein said container is selected from the list consisting of a blister pack, stick, bag, pouch or capsule.

Item 37. The container according to item 35 or 36 comprising one dose of said composition.

Item 38. A kit comprising a plurality of containers according to any one of items 35 to 37.

Item 39. A method for maintenance of oral health in a subject, said method comprising the step of
providing a therapeutic effective amount of a composition according to any of the proceeding items to a subject in the need thereof.

Item 40. The method according to item 39, wherein said composition comprises at least $10^7$ CFU Lactobacillus per daily dose, such as in the range of $10^7$ to $10^{10}$ CFU Lactobacillus per daily dose, such as $10^8$ to $10^9$ CFU Lactobacillus per daily dose.

Item 41. The method according to item 39 or 40, wherein said composition comprises Lactobacillus curvatus strain EB10 (DSM 32307).

Item 42. The method according to item 41, wherein said composition further comprises Lactobacillus rhamnosus strain PB01 (DSM 14870).

Item 43. The method according to any one of items 39 to 42, wherein said composition comprises at least $5\times10^7$ CFU Lactobacillus curvatus strain EB10 (DSM 32307) per daily dose.

Item 44. The method according to item 43, wherein said composition comprises at least $5\times10^7$ CFU Lactobacillus rhamnosus strain PB01 (DSM 14870) per daily dose.

Item 45. A method for reducing gingival inflammation in a subject, said method comprising the step of
providing a therapeutic effective amount of a composition according to any of the proceeding items to a subject in the need thereof.

Item 46. A method for reducing, alleviating or preventing a periodontal disease associated with gingival inflammation in a subject, said method comprising the step of
providing a therapeutic effective amount of a composition according to any of the proceeding items to a subject in the need thereof.

Item 47. A method for reducing gingival crevicular fluid in a subject, said method comprising the step of
providing a therapeutic effective amount of a composition according to any of the proceeding items to a subject in the need thereof.

EXAMPLES

Example 1

Bacterial Strains

Candidate probiotic strains

| Strain ID | | Deposit number |
|---|---|---|
| S1-P1 | Lactobacillus fermentum | |
| S1-P2 | Lactobacillus fermentum | |
| S1-P3 | Lactobacillus paracasei | |
| DSM15224 | nd | |
| P2-1 | Lactobacillus rhamnosus | |
| P2-2 | Lactobacillus curvatus | DSM 32307* |
| P2-3 | Lactobacillus curvatus | |
| P3-1 | Lactobacillus curvatus | |
| P3-2 | Lactobacillus curvatus | |
| P5-1 | Lactobacillus rhamnosus | |
| WCFS-1 | Lactobacillus plantarum | |
| PB01 | Lactobacillus rhamnosus | DSM 14870 |
| EB01 | Lactobacillus gasseri | DSM 14869 |
| LS33 | Lactobacillus salivarius strain JCM 1231 | ATCC SD5208 |

*Lactobacillus curvatus strain EB10 (also referred to herein as P2-2) was deposited with DSMZ-Deutsche Sammlung von Mikroorganismen und Zellkulturen GmbH (Braunschweig, Germany) on 4 May 2016 for the purposes of patent deposit according to the Budapest Treaty.

The strains S1-P1, S1-P2, S1-P3, P2-1, P2-2, P2-3, P3-1, P3-2, P5-1 was isolated from a mouth swap sample obtained from a healthy individual.

Six oral pathogen bacterial strains were used in the present in vitro study:

Two pathogen strains associated with caries: Streptococcus mutans ChDC YM31 16S ribosomal RNA gene (CCUG 17824) and Streptococcus gordonii (CCUG 25608).

Four pathogen strains associated with gingivitis: Porphyromonas gingivalis (ATCC 33277), Prevotella intermedia strain OH5061 (CCUG 27725), Aggregatibacter actinomycetemcomitans HK1651, and Fusobacterium nucleatum (ATCC 49256).

The two streptococci strains have been shown to be involved in the initiation and the development of dental caries. Especially S. mutans is one of the main indicator strains of an aciduric biofilm. P. intermedia and F. nucleatum both belong to the 'orange complex', which presence in the biofilm often precedes the bacteria in the 'red complex'. The red complex is found most frequently in deep periodontal pockets. P. gingivalis belongs to the 'red complex'. A. actinomycetemcomitans is associated with the development of the rare condition aggressive periodontitis. Both P. intermedia and P. gingivalis are believed to contribute to halitosis due to their production of volatile sulphur compounds.

Example 2

Agar Overlay Interference Assay

Cultivation

The lactobacilli of Example 1 were initially cultured for 16-20 h on MRS agar (Oxoid Ltd., Hampshire, UK). A distinct colony of each bacterium was then transferred to 4.5 ml MRS (Oxoid Ltd., Hampshire, UK) broth for a further 16-20 h of incubation. The pathogens were cultured on TSA plates (Oxoid Ltd., Hampshire, UK) supplemented with cysteine, menadione and horse blood for 16-20 h, and on the following day, pure colonies of each bacterium were transferred to 2 ml BHI broth (Oxoid Ltd., Hampshire, UK) and incubated for another 16-20 h. Culturing of the bacteria was performed in anaerobic chamber at 37°.

Agar Overlay Interference Tests

The optical density of the broth cultures of lactobacilli were adjusted to 1.8 at 630 nm (Genesis 10 uv, Thermo Scientific, Madison, Wis., USA). The cultures were then serial diluted in 10-fold steps. The undiluted suspensions and cell suspensions corresponding to $10^5$, $10^3$ and $10^1$ CFU/ml were used in the inhibition assay. One millilitre of each lactobacilli suspension was added to 24 ml molten sterile MRS agar (approximately 45° C.) and plates were casted. Plates with no lactobacilli added were used as control plates. When the agar was set, the plates were incubated overnight in an anaerobic atmosphere. The next day (after 20 h) a second layer of 23 ml TSA agar (Oxoid Ltd., Hampshire, UK) supplemented with cysteine, menadione and horse blood was casted on top of the MRS agar with grown lactobacilli. The plates were allowed to dry for 3 h at room temperature. Broth cultures of the pathogens grown in BHI broth were diluted with the same medium and the OD was measured at 500 nm and adjusted to 0.2. The suspensions of the pathogens were stamped on the plates with Steer's replicator (CMI-Promex ICN, Pedricktown, N.J., USA). The plates were left at room temperature for 1 h to dry and were subsequently incubated overnight at 37° C. in the anaerobic chamber. The growth of the pathogens on the plates with lactobacilli added was then compared to that of the control plates. The results of the agar overlay test were categorized according to Simark-Mattsson et al. [2007]: score 0=complete inhibition (no visible colonies), score 1=slight inhibition (at least one visible colony but definitely smaller amounts than on the control plate) and score 2=no inhibition (the same growth as on the control plate). The evaluation of the plates was performed by two independent observers, in cases of disagreement a consensus was reached after discussion. All growth inhibition assays were repeated on three different occasions.

Results from agar overlay interference on the pathogen strains of *Streptococcus mutans* and *Streptococcus gordonii*.

|  | S. mutans | | | S. gordonii | | |
|---|---|---|---|---|---|---|
|  | $10^1$ | $10^3$ | $10^5$ | $10^1$ | $10^3$ | $10^5$ |
| Control |  | ++ |  |  | + |  |
| S1-P1 | 0 | 0 | 0 | 0 | 0 | 0 |
| S1-P2 | 1 | 0 | 0 | 0 | 0 | 0 |
| S1-P3 | 1 | 0 | 0 | 1 | 0 | 0 |
| DSM15224 | 1 | 1 | 0 | 0 | 0 | 0 |
| P2-1 | 2 | 0 | 0 | 1 | 0 | 0 |
| P2-2 | 1 | 0 | 0 | 0 | 0 | 0 |
| P2-3 | 2 | 0 | 0 | 2 | 0 | 0 |
| P3-1 | 1 | 0 | 0 | 1 | 0 | 0 |
| P3-2 | nd | 1 | 0 | nd | 0 | 0 |
| P5-1 | 1 | 0 | 0 | 0 | 0 | 0 |
| WCFS-1 | 0 | 0 | 0 | 0 | 0 | 0 |
| PB01 | 1 | 0 | 0 | 0 | 0 | 0 |
| EB01 | 2 | 1 | 0 | 2 | 0 | 0 |
| LS33 | 0 | 0 | 0 | 0 | 0 | 0 |

Results from agar overlay interference on the pathogen strains of *Prevotella intermedia* strain, *Aggregatibacter actinomycetemcomitans*, and *Fusobacterium nucleatum*.

|  | P. intermedia | | | A. actinom | | | F. nucleatum | | |
|---|---|---|---|---|---|---|---|---|---|
|  | $10^1$ | $10^3$ | $10^5$ | $10^1$ | $10^3$ | $10^5$ | $10^1$ | $10^3$ | $10^5$ |
| Control |  | + |  |  | + |  |  | + |  |
| S1-P1 | 0 | 0 | 0 | 0 | 0 | 0 | 0 | 0 | 0 |
| S1-P2 | 1 | 0 | 0 | 0 | 0 | 0 | 2 | 0 | 0 |
| S1-P3 | 1 | 0 | 0 | 1 | 0 | 0 | 2 | 0 | 0 |
| DSM15224 | 0 | 0 | 0 | 0 | 0 | 0 | 1 | 0 | 0 |
| P2-1 | 1 | 0 | 0 | 0 | 0 | 0 | 2 | 0 | 0 |
| P2-2 | 0 | 0 | 0 | 0 | 0 | 0 | 0 | 0 | 0 |
| P2-3 | 1 | 0 | 0 | 1 | 0 | 0 | 2 | 0 | 0 |
| P3-1 | 1 | 0 | 0 | 0 | 0 | 0 | 0 | 0 | 0 |
| P3-2 | nd | 0 | 0 | nd | 0 | 0 | nd | 0 | 0 |
| P5-1 | 0 | 0 | 0 | 0 | 0 | 0 | 0 | 0 | 0 |
| WCFS-1 | 0 | 0 | 0 | 0 | 0 | 0 | 0 | 0 | 0 |
| PB01 | 0 | 0 | 0 | 0 | 0 | 0 | 0 | 0 | 0 |
| EB01 | 2 | 0 | 0 | 2 | 0 | 0 | 2 | 0 | 0 |
| LS33 | 0 | 0 | 0 | 0 | 0 | 0 | 0 | 0 | 0 |

Example 3

Immunomodulation—In Vitro Study

Immature monocyte-derived dendritic cells from three different donors were exposed to the probiotic candidates of Example 1 at 100 µg/mL, in culture for 24 hours. The probiotic bacterial strain *Lactobacillus acidophillus* NCFM (ATCC 700396) was included as reference. Subsequently, in cell culture supernatants, the probiotic-induced IL-10 and IL-12 secretions, respectively, were measured using ELISA.

An earlier study has shown that the in vitro probiotic immune modulation of the IL10/12 balance is predictive for the protective effect in vivo in a TNBS-induced mouse model of colitis (B. Foligne et al., World J Gastroenterol 2007, 13:236-243). This correlation has been confirmed by others and has shown general value to predict potential anti-inflammatory modulation mediated by probiotics.

The IL10/12 ratios of a panel of probiotic candidate strains obtained by assaying on immature monocyte-derived dendritic cells from three different donors are presented in FIG. 1.

The data shows that nine strains out of the 14 strains assayed displayed a ratio of IL10/12 above 5 and four strains displayed a ratio of IL10/12 above 50.

Figure 2:
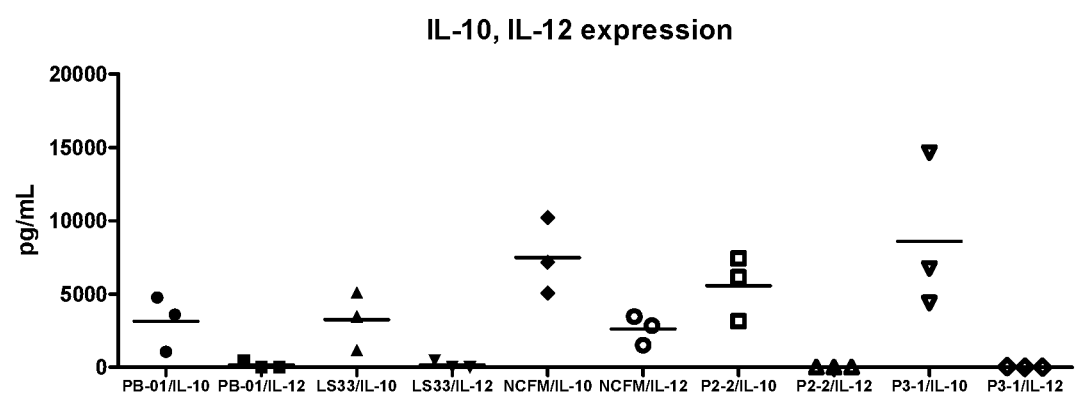
FIG. 2 shows the IL10 and IL12 expression induced by selected probiotic candidate strains (PB-01, L33, P2-2 and P3-1) assaying on immature monocyte-derived dendritic cells from three different donors. The NCFM is included as reference. For further details see Example 3.
Figure 3:
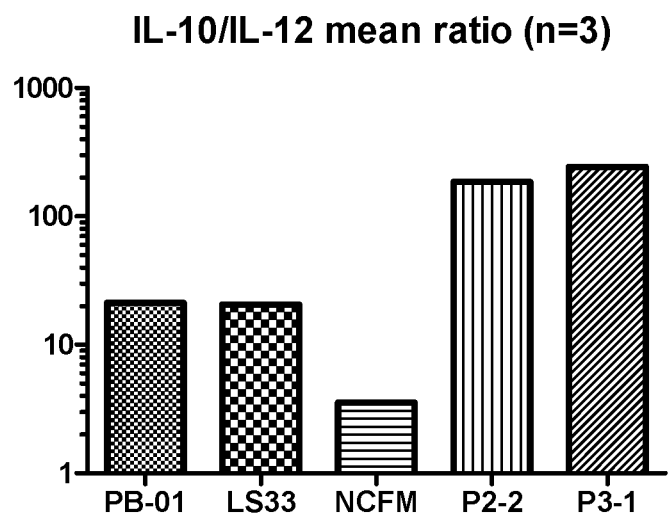
FIG. 3 shows the IL10/12 ratios obtained by the selected probiotic candidate strains (PB-01, L33, P2-2 and P3-1) assaying on immature monocyte-derived dendritic cells from three different donors. For further details see Example 3.

The data obtained PB01, P2-2, P3-1, LS33 and NCFM is presented in further details in FIGS. 2 and 3. The data demonstrated that the IL10/12 ratios were very much the same (mean ~20) in the supernatants of PB01 and LS33 probiotics in contrast to the low ratio found in the supernatant of NCFM (triplicate measurements). The IL10/12 balance in the P2-2 and P3-1 were even more pronounced than PB01 and LS33 reaching levels above 100.

In the study by Foligne et al., in supernatants of PBMCs treated for 24 hours with LS33, the relatively high ratio of IL10/12 (median ~20) correlated with a protective effect in a mouse colitis model as compared to NCFM, which in vitro induced a low IL-10/12 ratio (median ~2) and in vivo offered no protection.

The present in vitro suggests that PB01, P2-2 and P3-1 may exert the same anti-inflammatory properties as shown for LS33, since both probiotics in vitro induce immature dendritic cells to secrete similar IL-10 and IL-12 levels.

Example 4

Clinical Trial Study

Aim

The aim of the study was to investigate the effect of tablets containing probiotic candidate strains on the degree of gingival inflammation.

Study Design

The study was planned and conducted as a double-blind placebo-controlled randomized trial with two parallel arms. The intervention period was planned to be 4 weeks. The study plan was submitted for ethical approval.

Study Group

The participants were recruited among patients at the clinic at School of Dentistry and through www.forsogsperson.dk. 50 participants between 18 and 50 years were invited and enrolled after verbal and written information. After informed consent, participants were randomly allocated to either the probiotic group or the placebo group with aid of a computer program.

The inclusion criteria were:
i) presence of at least two buccal marginal sites with moderate to severe gingival inflammation and with a probing depth of ≤5 mm
ii) bleeding on probing (BOP)

The exclusion criteria was
i) habitual intake of probiotic bacteria
ii) smoking on regular basis
iii) pregnancy
iv) intake of antibiotics within the last two months before baseline
v) low stimulated saliva rate (0.8 ml/min)
vi) active decay with several untreated open caries lesions.

Methods

Intervention: After informed consent, baseline examination and sampling, participants were randomly assigned to one of the study groups and given supply of either probiotic tablets or placebo tablets.

The probiotic tablets contained *Lactobacillus rhamnosus* PB01 and *Lactobacillus curvatus* EB10 at a dose of $10^9$ CFU/tablet. The placebo tablets were identical in size and composition but without the addition of the probiotic strains. Both tablets were provided by Bifodan A/S. The participants were instructed to take one tablet in the morning and one in the evening thirty minutes after tooth brushing. The tablets were packed in identical pots with color coding. The code will be kept from the investigators until the analysis are finished.

After baseline registration, participants were instructed to take two tablets a day for four weeks and they were asked to keep a logbook of the intake. Follow up registrations were conducted after two weeks, four weeks and six weeks.

Clinical procedures: At each visit, GCF was collected and plaque index (PI), gingival index (GI), and bleeding on probing (BOP) was registered.

GCF: For the collection of GCF, two contralateral buccal sites from the upper incisors, canines or premolars was selected from each participant. Visual supragingival plaque on the selected teeth was removed and the sites were dried with cotton pellets. GCF was collected using periopaper strips (ProFlow, Amityville, N.Y., USA) gently inserted in the gingival sulcus for 20 s. The volume of GCF was recorded using a Peritron 8000 (Proflow) and expressed in μL. The strips were then transferred to plastic tubes and stored at −80 until further analysis.

Statistical methods: All data was processed with SPSS software (v 22.0; Chicago, Ill., USA). The follow-up values were compared to baseline within each group by Wilcoxon paired two-sided test and differences between groups were analyzed by Wilcoxon unpaired test. Categorical data were compared with chi-square tests. A p-value <0.05 is considered statistical significant.

Scientific Importance

Figure 4:
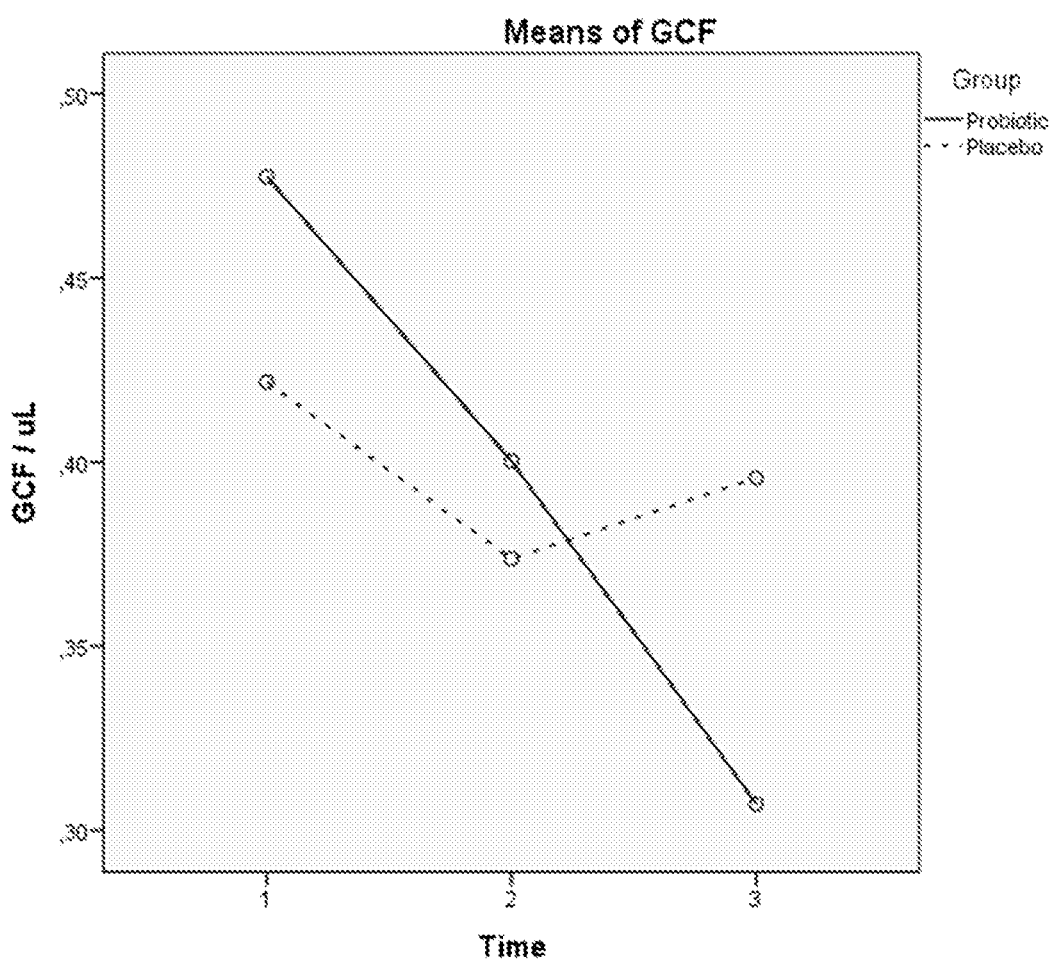
FIG. 4 shows the volume of gingival crevicular fluid (GCF) as function of time of the intervention (probiotic vs placebo). For further details, see Example 4 (in vivo study). 1: Baseline, 2: two weeks, 3: three weeks.
Figure 6:
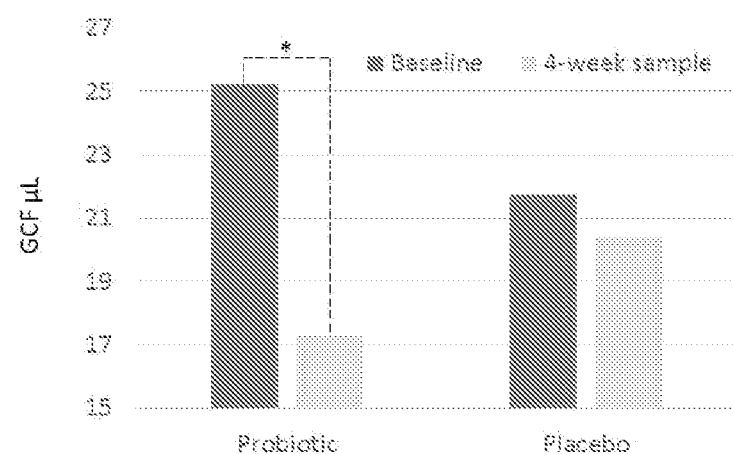
FIG. 6 shows the effect of the probiotic composition on the gingival crevicular fluid compared to placebo treatment. The asterisk (*) denotes the application of a two way mixed model ANOVA, which confirms that there is a statistically significant interaction between the intervention and time on GCF, $p<0.05$.

The data demonstrate that is a statistically significant interaction between the intervention and time on GCF, p<0.05 (two way mixed model ANOVA), see FIG. 4 and FIG. 6.

The study thus provides evidence that the probiotic tablets influences at least one clinical marker of gingival inflammation and/or pro- and anti-inflammatory cytokines which can lead to new supplementary treatment of gingivitis.

Example 5

Tablet

| COMPOSITION | | |
|---|---|---|
| Active substances | | |
| Name of constituent | Added per tablet (mg) | Function | Reference to Standards |
| Freeze dried culture of *Lactobacillus Rhamnosus* PB01 | At least $10^9$ CFU Lactobacilli in total | Active ingredient | Microbial Culture Internal 04/30/01613 |
| Freeze dried culture of *Lactobacillus curvatus* EB10 | | Active ingredient | Microbial Culture Internal 04/30/01724 |
| Excipient in descending order | | |
| Xylitol | Bulking agent | Food additive |
| Microcrystalline cellulose | Bulking agent | |
| Isomalt | Bulking agent | Food Additive, E953 |
| mono- and diglyceride of fatty acids | Glazing agent | Food Additive, E471 |
| Lemon flavour | Flavour | Natural flavour |
| Maltodextrin | Binder | Food additive |
| Sodium carboxymethylcellulose | Binder | Food additive |
| Citric acid | Flavour | Food additive |
| Silicon dioxide | Glazing agent | Food additive |
| Steviol glycoside | Sweetness | Food Additive, E960 |

Example 6

Characterization of Bacterial Strains

Figure 5:
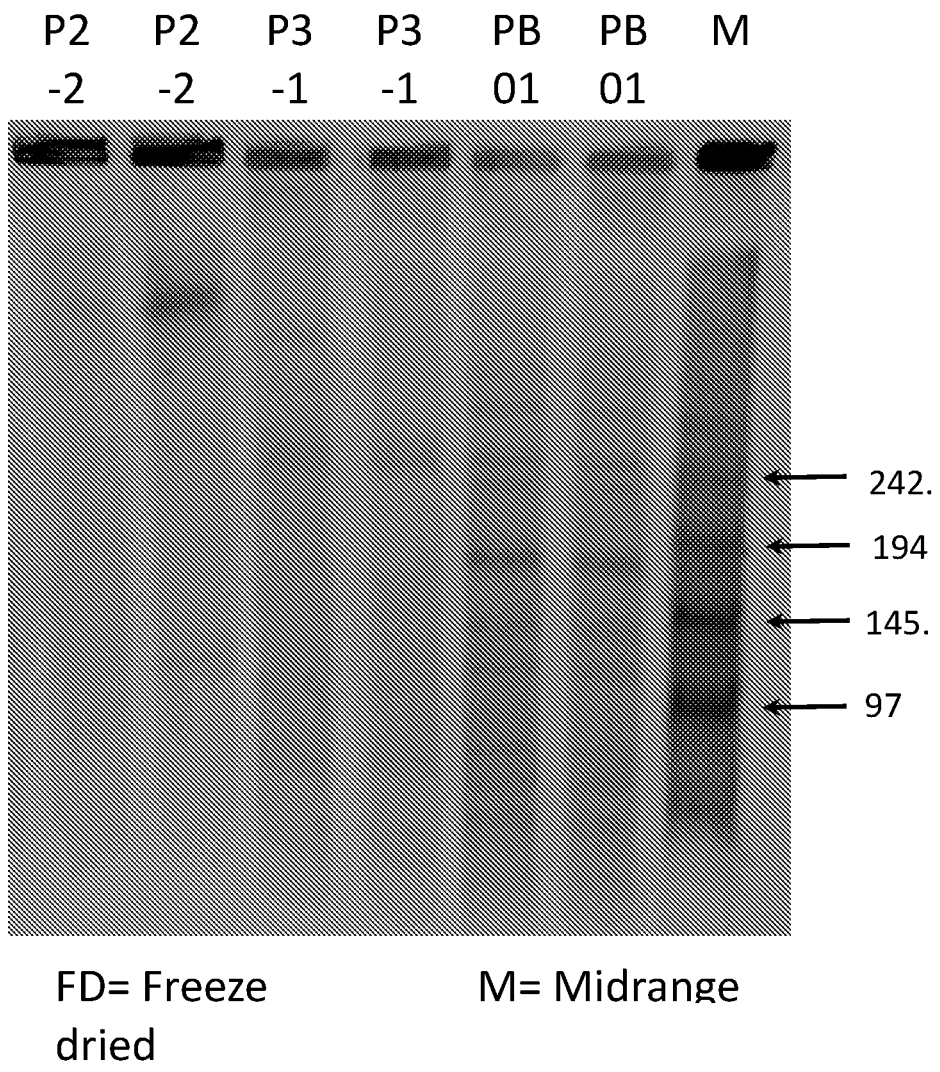
FIG. 5 shows AscI digestion (50 U over night at 37° C.) of genomic DNA isolated from the bacterial strain *Lactobacillus curvatus* denoted P2-2 (deposited with DSMZ-Deutsche Sammlung von Mikroorganismen and Zellkulturen GmbH (Braunschweig, Germany) on 4 May 2016 under the strain name *Lactobacillus curvatus* strain EB10—deposit number DSM 32307).

DNA isolated from the bacterial strain *Lactobacillus curvatus* denoted P2-2 (also referred herein as EB10), *Lactobacillus curvatus* P3-1 and *Lactobacillus rhamnosus* strain PB01 (DSM 14870) was digested over night at 37° C. with 50 U of AscI digestion. The AscI digested DNA was loaded on a 1.1% agarose and run in 0.5× TBE buffer (Pulse time: 2-30 s, 5.3 V/cm). The results are shown in FIG. 5.

Example 7

Suppression of Th1 and Th17 Response

Human dendritic cells were established from three different donors according to procedures previously described (Gad et al. FEMS Immunol Med Microbiol 2011, 63:93-

Figure 7:
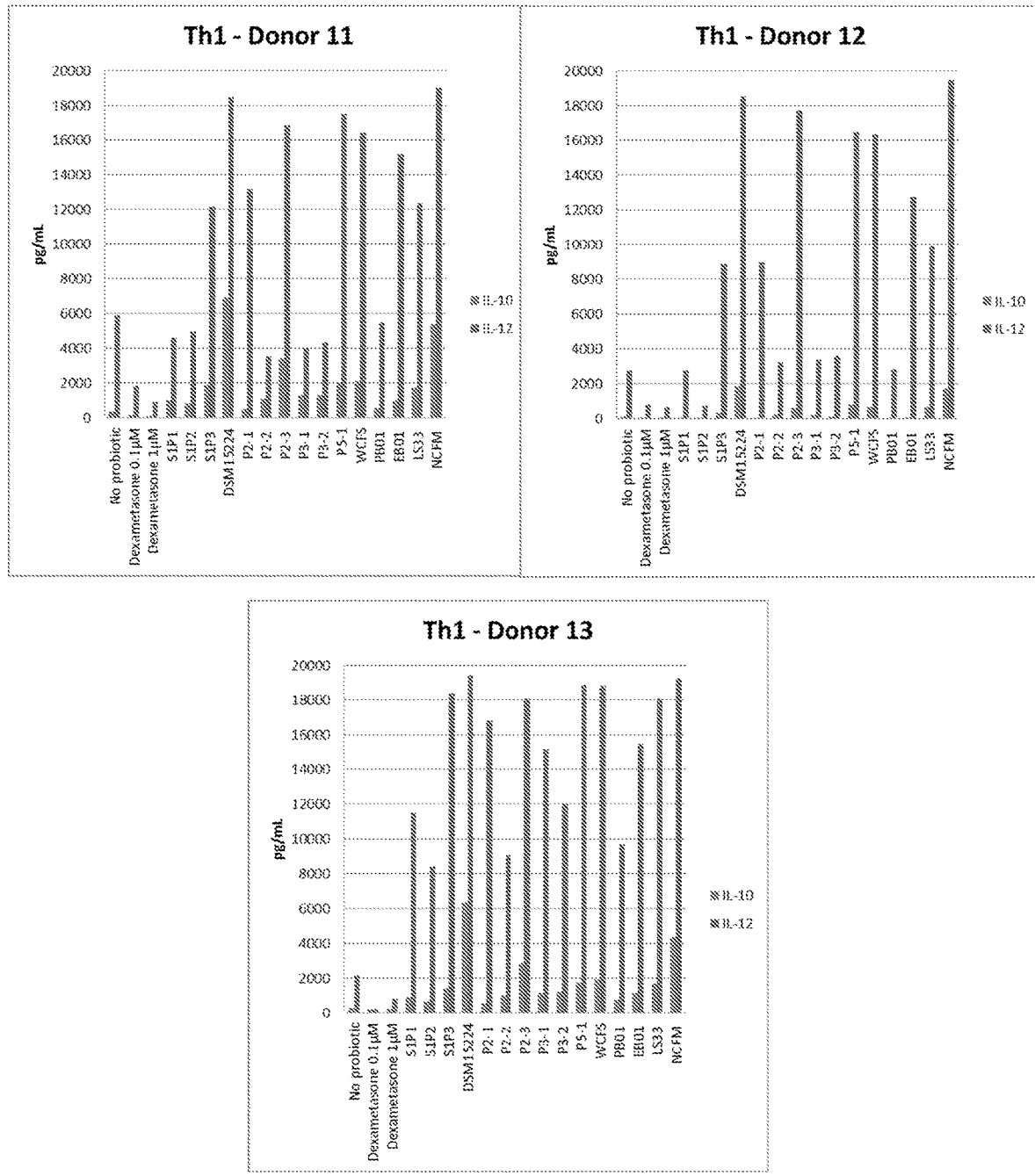
FIG. 7 shows the results of ELISA measurements of IL10 (left bar) and IL12p70 (right bar) after exposure to different probiotic strains and subsequent cocktail induced Th1-response.
Figure 10:
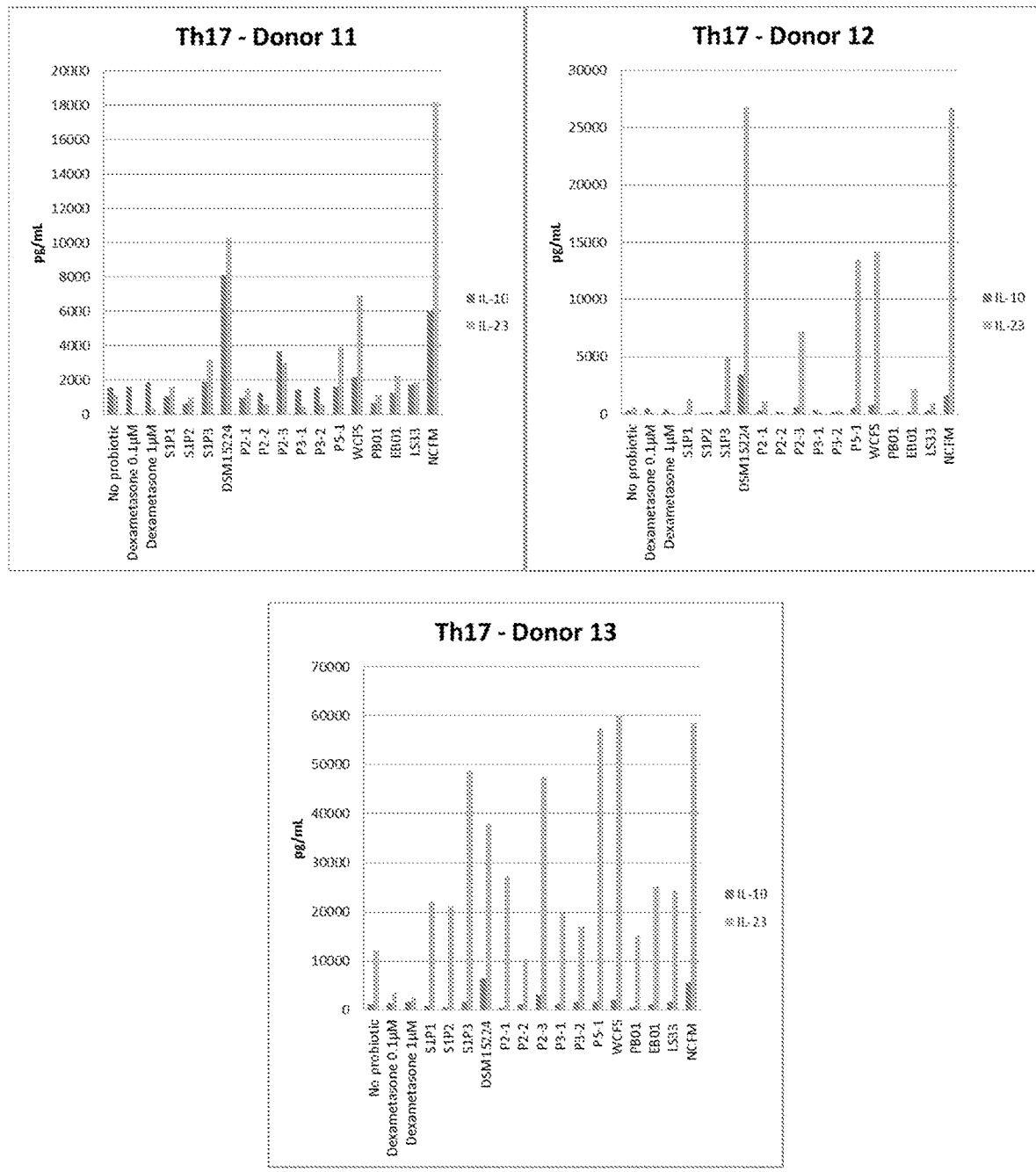
FIG. 10 shows the results of ELISA measurements of IL10 (left bar) and IL23 (right bar) after exposure to different probiotic strains and subsequent cocktail induced Th17-response.

107). The ability of the probiotic strains to inhibit or reduce cocktail-induced pro-inflammatory Th1- and Th17-responses were measured according to the procedures previously described (Gad et al. FEMS Immunol Med Microbiol 2011, 63:93-107; Jensen & Gad, Journal of Inflammation 2010, 7:37). The probiotic strains (100 µg freezed dried pellet) were exposed to dendritic cells for 6 hours, after which a Th1-cocktail (Gad et al. FEMS Immunol Med Microbiol 2011, 63:93-107) or a Th17-cocktail (Jensen & Gad, Journal of Inflammation 2010, 7:37) was added and incubated for 24 hours. As controls in these experiments dendritic cells not exposed to the probiotic strains were used. After 24-hour incubation, the secretion of IL-10 and IL-12p70 was measured in relation to the Th1-response, and IL-23 and IL-12p70 in relation to the Th17 response was measure by ELISA as previously described (Gad et al. FEMS Immunol Med Microbiol 2011, 63:93-107). The results of these measurements for the three donors are shown in FIG. 7 and FIG. 10, respectively.

To evaluate the potential of the probiotic strains' ability to reduce either a Th1 or a Th17 pro-inflammatory response the following criteria were defined. A high IL-10/IL12p70 ratio after exposure to immature DC is wanted. After probiotic exposure and subsequent cocktail induced Th1 response, a low IL12p70 level and an increased IL-10/IL12p70 ratio is wanted. After probiotic exposure and subsequent cocktail induced Th17 response, a low level of IL23 and an increased IL-10/IL-23 is wanted. The fulfillment of these criteria were subsequently scored as presented in the table of FIG. 11, with samples without probiotic exposure as reference.

Figure 8:
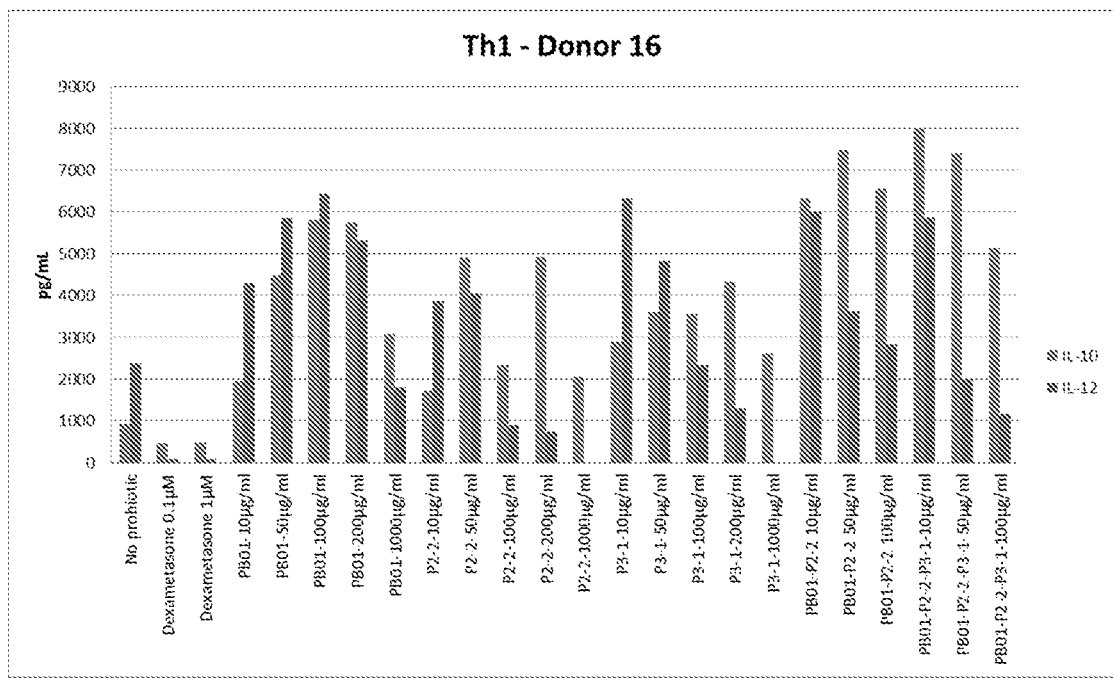
FIG. 8 shows the results of ELISA measurements of IL10 (left bar) and IL12p70 (right bar) after exposure to probiotic strains in different doses and mixes and subsequent cocktail induced Th1-response (Donor-16).
Figure 9:
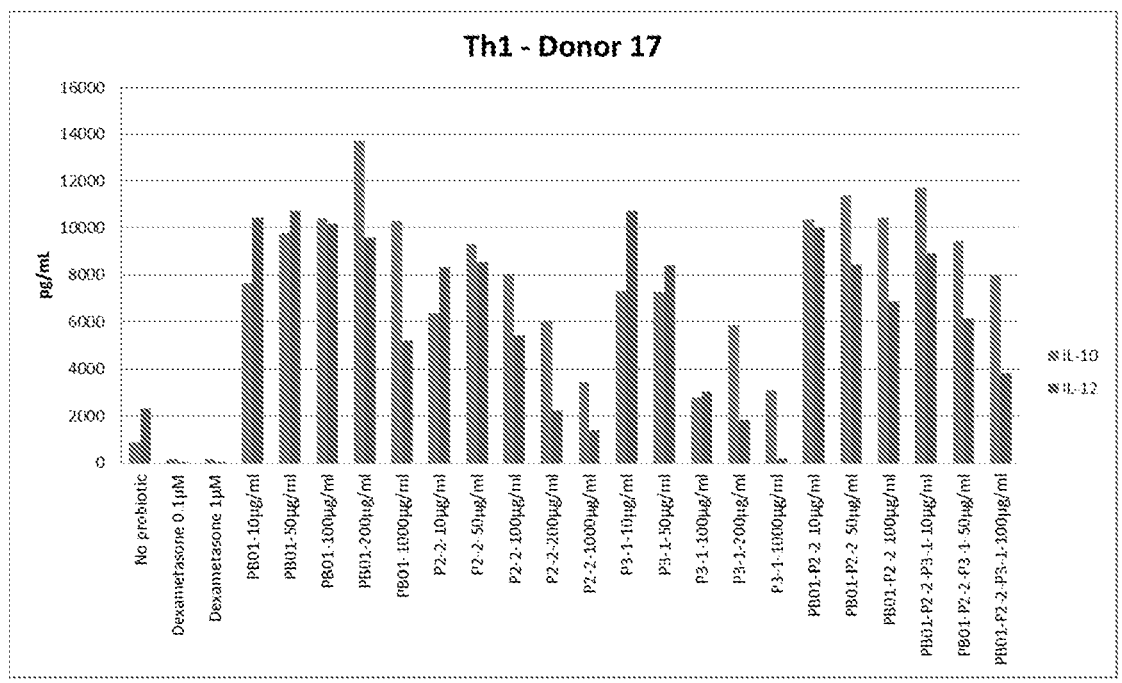
FIG. 9 shows the results of ELISA measurements of IL10 (left bar) and IL12p70 (right bar) after exposure to probiotic strains in different doses and mixes and subsequent cocktail induced Th1-response (Donor-17).

In addition to these experiment a dose-response study was also performed with selected strains (P2-2, P3-1 and PB01) looking at the effect of probiotic dose and the effect of mixing strains on the ability to reduce the cocktail-induced Th1-response. The result of this experiment in two different donors is shown in FIG. 8 and FIG. 9.

REFERENCES

Reid G, Younes J A, Van der Mei H C, Gloor G B, Knight R, Busscher H J. Microbiota restoration: natural and supplemented recovery of human microbial communities. Nat Rev Microbiol. 2011; 9: 27-38.
Twetman S, Keller M K. Probiotics for caries prevention and control. Adv Dent Res. 2012; 24: 98-102.
Twetman S, Derawi B, Keller M, Ekstrand K, Yucel-Lindberg T, Stecksen-Blicks C. Short-term effect of chewing gums containing probiotic *Lactobacillus reuteri* on the levels of inflammatory mediators in gingival crevicular fluid. Acta Odontol Scand. 2009; 67: 19-24.
Ericson D, Hamberg K, Bratthall G, Sinkiewicz-Enggren G, Ljunggren L. Salivary IgA response to probiotic bacteria and mutans streptococci after the use of chewing gum containing *Lactobacillus reuteri*. Pathog Dis. 2013; 68: 82-7.

The invention claimed is:

1. A *Lactobacillus curvatus* strain EB10 (DSM 32307), wherein said strain is in a lyophilized or spray dried form.

2. A culture comprising the *Lactobacillus curvatus* strain EB10 (DSM 32307) of claim 1, wherein said culture is in a lyophilized or spray dried form.

3. The culture according to claim 2, further comprising at least one additional *Lactobacillus* sp.

4. A composition comprising the *Lactobacillus curvatus* strain EB10 (DSM 32307) of claim 1.

5. The composition according to claim 4, further comprising at least one additional *Lactobacillus* sp.

6. The composition according to claim 4, wherein said composition comprises from $10^5$ to $10^{13}$ CFU of the *Lactobacillus curvatus* strain EB10 (DSM 32307) of said composition.

7. The composition according to claim 5, wherein said composition comprises at least $10^7$ CFU *Lactobacillus curvatus* strain EB10 (DSM 32307) per gram of said composition and at least $10^7$ CFU *Lactobacillus rhamnosus* strain PB01 (DSM 14870) per gram of said composition.

8. The composition according to claim 4, wherein said composition is a tablet, capsule, powder, effervescent tablet, effervescent powder, granulate, microencapsulated product, suspension, spray, gel or cream.

9. A method of inhibiting inflammation in the oral cavity of a subject comprising administering the composition of claim 4 to said subject.

10. The method according to claim 9, wherein said inflammation is presented in said subject as gingivitis or periodontitis.

11. The method according to claim 9, wherein said composition comprises from $10^7$ to $10^{10}$ CFU *Lactobacillus curvatus* strain EB10 (DSM 32307) per daily dose.

12. The method according to claim 9, wherein said composition comprises at least $5\times10^7$ CFU *Lactobacillus curvatus* strain EB10 (DSM 32307) per daily dose and at least $5\times10^7$ CFU *Lactobacillus rhamnosus* strain PB01 (DSM 14870) per daily dose.

13. The composition according to claim 4, wherein said composition is a nutraceutical or nutritional supplement.

14. A method for maintaining the oral health in a subject, said method comprising providing the composition according to claim 4 to said subject.

15. The culture of claim 3, wherein the at least one additional *Lactobacillus* sp. is *Lactobacillus rhamnosus* strain PB01 (DSM 14870).

16. The composition of claim 5, wherein the at least one additional *Lactobacillus* sp. is *Lactobacillus rhamnosus* strain PB01 (DSM 14870).

17. The composition according to claim 4, wherein said composition comprises at least one excipient.

18. The composition according to claim 17, wherein said at least one excipient is selected from the group consisting of a bulking agent, a binder, a glazing agent, a sweetener and a flavour.

19. The composition according to claim 18, wherein said bulking agent is at least one bulking agent selected from the group consisting of xylitol, sorbitol, erythritol, maltitol, lactitol, inositol and mannitol microcrystalline cellulose and isomalt.

20. The composition according to claim 18, wherein said binder is at least one binder selected from the group consisting of maltodextrin and sodium carboxymethylcellulose.

21. The composition according to claim 18, wherein said glazing agent is at least one glazing agent selected from the group consisting of mono- and diglyceride of fatty acids, silicon dioxide, stearic acid, beeswax, candelilla wax, carnauba wax, shellac, microcrystalline wax, crystalline wax, lanolin, oxidized polyethylene wax, esters of colophonium, and paraffin.

22. The composition according to claim 18, wherein said sweetener is at least one sweetener selected from the group consisting of stevia, a steviol glycoside such as stevioside and rebaudioside, aspartame, sucralose, neotame, acesulfame potassium (Ace-K), saccharin, and advantame.

23. The composition according to claim 18, wherein said flavour is at least one flavour selected from the group consisting of citric acid, lemon flavour, honeydew melon flavour, blueberry flavour, peach flavour, strawberry flavour, raspberry flavour, cola flavour, chocolate flavour, peppermint flavour, cherry flavour, lime flavour, orange flavour, vanilla flavour, tangerine flavour, liquorice flavour, apricot flavour, eucalyptus flavour, green tea flavour, ginger flavour and bilberry flavour.

\* \* \* \* \*